United States Patent
Dschietzig

(10) Patent No.: US 10,842,851 B2
(45) Date of Patent: Nov. 24, 2020

(54) RELAXIN FOR TREATING PATIENTS AFFLICTED OF IMPAIRED GLUCOSE TOLERANCE

(71) Applicants: Immundiagnostik AG, Bensheim (DE); Thomas Dschietzig, Berlin (DE)

(72) Inventor: Thomas Dschietzig, Berlin (DE)

(73) Assignee: Immundiagnostik AG, Bensheim (DE)

(*) Notice: Subject to any disclaimer, the term of this patent is extended or adjusted under 35 U.S.C. 154(b) by 0 days.

(21) Appl. No.: 14/380,163

(22) PCT Filed: Feb. 22, 2013

(86) PCT No.: PCT/EP2013/053633
§ 371 (c)(1),
(2) Date: Aug. 21, 2014

(87) PCT Pub. No.: WO2013/124463
PCT Pub. Date: Aug. 29, 2013

(65) Prior Publication Data
US 2015/0038411 A1 Feb. 5, 2015

(30) Foreign Application Priority Data
Feb. 22, 2012 (EP) .................................... 12156442

(51) Int. Cl.
*A61K 38/22* (2006.01)
*A61K 9/00* (2006.01)
*A61K 9/16* (2006.01)

(52) U.S. Cl.
CPC ........ *A61K 38/2221* (2013.01); *A61K 9/0019* (2013.01); *A61K 9/1647* (2013.01)

(58) Field of Classification Search
None
See application file for complete search history.

(56) References Cited

U.S. PATENT DOCUMENTS

| 5,134,122 A | 7/1992 | Orsolini |
| 2005/0238639 A1 | 10/2005 | Conrad et al. |
| 2006/0281669 A1 | 12/2006 | Yue |
| 2011/0039778 A1* | 2/2011 | Barlos .................... C07K 14/64 514/12.7 |

OTHER PUBLICATIONS

Bathgate et al. (Relaxin Family Peptides and Their Receptors; Physiol. Rev 93: 405-480, 2013).*
Phillips et al. ("The Metabolic Syndrome and Glucose Intolerance" Hospital Physician Jul. 2006).*
Qu et al. ("The definition of insulin resistance using HOMA-IR for Americans of Mexican descent using machine learning" PLOS ONE;Jun. 2011 vol. 6, Issue 6).*
J. M. Olefsky et al., "Potentiation of Insulin Binding and Insulin Action by Purified Porcine Relaxin", Annals of the New York Academy of Sciences, vol. 380, 1982, pp. 200-216.
Lisa Gittens et al., "Pregnant Women Lacking Circulating Relaxin have Decreased Insulin Sensitivity", American Journal of Obstetrics and Gynecology, vol. 184, No. 1, Jan. 2001, p. S64.
Barbara Szepietowska et al.,"Plasma Relaxin Concentration is Related to Beta-Cell Function and Insulin Sensitivity in Women with Type 2 Diabetes Mellitus", Diabetes Research and Clinical Practice, vol. 79, No. 3, Nov. 26, 2008, pp. E1-E3.

* cited by examiner

*Primary Examiner* — James H Alstrum-Acevedo
*Assistant Examiner* — Tara L Martinez
(74) *Attorney, Agent, or Firm* — Blank Rome LLP

(57) ABSTRACT

A pharmaceutical composition for treatment for of r afflicted or in risk of becoming of impaired glucose tolerance (IGT) and/or type-2 it comprising an effective amount of relaxin for protecting beta-cells and beta-cell function against the effects of high blood glucose (glucotoxicity). Treatment of persons of disglycaemias, and protection of beta cells of the islets of Langerhans and beta-cell function in patients having type-2 diabetes, is diclosed.

2 Claims, 3 Drawing Sheets

Friedman ANOVA on ranks, followed by Dunnett's test

Friedman ANOVA on ranks, followed by Dunnett's test

RELAXIN FOR TREATING PATIENTS AFFLICTED OF IMPAIRED GLUCOSE TOLERANCE

FIELD OF THE INVENTION

The present invention relates to pharmaceutical compositions and methods for treating human subjects in risk of becoming afflicted with impaired glucose tolerance (IGT).

BACKGROUND OF THE INVENTION

Diabetes mellitus is a group of metabolic diseases in which a person has high blood sugar (i. e. glucose), either because the body does not produce enough insulin, or because cells do not respond to the insulin that is produced. The high blood sugar produces the classical symptoms of polyuria, polydipsia and polyphagia. There are three main types of diabetes: Type-1 diabetes results from the body's failure to produce insulin. Type-1 diabetes is also referred to as insulin-dependent diabetes mellitus (IDDM) or juvenile diabetes. Type-2 diabetes results from a condition in which cells fail to use insulin properly or have become "resistant" to insulin. Insulin resistance (IR) in muscle and fat cells reduces glucose uptake and its local storage as glycogen or triglycerides whereas insulin resistance in liver cells results in reduced glycogen synthesis and storage and a failure to suppress glucose production and release into the blood. If insulin resistance exists more insulin needs to be secreted by the pancreatic beta-cells. When this compensatory increase of insulin can no longer compensate for the "insulin resistance" (IR) blood glucose concentrations both after fasting and after glucose load increase and impaired glucose tolerance (IGT) occurs with moderately elevated blood glucose levels in first place and type-2 diabetes with markedly elevated blood glucose thereafter. Type-2 diabetes is also referred to as obesity-related diabetes, adult-onset diabetes or non-insulin-dependent diabetes mellitus (NIDDM). Other forms of diabetes mellitus include congenital diabetes due to genetic defects of insulin secretion, gestational diabetes when women have a high blood glucose level during pregnancy, cystic fibrosis-related diabetes, steroid diabetes induced by high doses of glucocorticoids, forms of monogenic diabetes, and latent autoimmune diabetes of adults (LADA).

Diabetes mellitus is a chronic, slowly progressive disease which cannot be cured except in very specific situations. Type-1 diabetes requires the person to inject insulin. Type-2 diabetes may be controlled by oral medications as well as possibly insulin. The established therapeutic options show however substantial adverse effects such as weight gain, lactate acidosis, hypoglycaemia or have relevant contraindications (thiazolidindiones: heart failure; glinides, sulfonylureas and their analogues and metformin: chronic renal failure; gliptines (DPP-4-inhibitors): generally not recommended for chronic renal failure). On the other hand, hyperglycaemia and insulin resistance are strong independent predictors of heart failure, renal failure, and cardiovascular mortality. Thirty percent of all type-2 diabetes patients develop diabetic nephropathy 10 to 15 years after diagnosis and onset of oral medications. Currently, metformin is recommended as a first line treatment of type-2 diabetes in overweight people as it decreases overall mortality when compared with insulin and sulfonylureas (glibenclamide and chlorpropamide) or with a group given dietary advice only. Metformin is also used in the treatment of other diseases associated with insulin resistance such as polycystic ovary syndrome (PCOS), non-alcoholic fatty liver disease (NAFLD) and premature puberty. However, metformin reduces hyperglycaemia primarily by suppressing glucose production by the liver (hepatic gluconeogenesis) and it appears to decrease mortality primarily through decreasing heart attacks, strokes and other cardiovascular complications. US 2006/281669 A1 (Yue S K), US 2005/238639 A1 (Conrad K P) disclose compositions comprising relaxin for ameliorating diabetes-related conditions, say for treating the negative cardiovascular effects of type-2 diabetes. Until now, none of these remedies was reported to cease the progression of metabolic dysglycaemia or diabetic disease (UKPDS Study, Lancet 1998; 352: 854-662). FIG. 4 depicts graphs of representative $HbA_{1c}$ values (glycosylated N-terminal valine in the beta-chain of haemoglobin) found in persons with manifest type-2 diabetes in dependence of years of medication with various medicaments.

It is therefore obvious to a skilled person that the state of the art represents a problem.

SUMMARY OF THE INVENTION

The present disclosure relates to a pharmaceutical composition for administration of a therapeutically effective amount or dose of relaxin to a person suffering from impaired glucose tolerance (IGT) or particularly in risk of becoming afflicted of impaired glucose tolerance (IGT) and insulin resistance (IR) which are usually followed by type-2 diabetes.

Persons particularly in risk of becoming afflicted of type-2 diabetes often have a body mass index (BMI) of greater 25 (overweight persons) or 30 (obese persons) and/or a sedentary life style. Severely obese persons having a BMI of greater 35 are also severely in risk of type-2 diabetes. Seemingly healthy people are in risk of type-2 diabetes when afflicted with impaired glucose tolerance (IGT) or a state of dysglycaemia which induces the pancreas to produce more insulin to compensate for impaired glucose tolerance (IGT) and insulin resistance (IR).

Relaxin has been well defined in its natural human form, animal form, and in its synthetic forms. In this disclosure, the term relaxin includes in its meaning "relaxin," "human relaxin", "native relaxin", and "synthetic relaxin," as well as "modified human relaxin" and "human relaxin analogues" unless not indicated otherwise. The term "relaxin" shall therefore include relaxin polypeptides as isolated from vertebrates such as pigs, rats, horses, or shark or isolated from milk or relaxin polypeptides produced by recombinant techniques based on cDNA clones encoding relaxin from mammals and other vertebrates. The term "relaxin" shall also refer to preprorelaxin, prorelaxin and relaxin analogues, derivatives of relaxin, chimeric peptides with relaxin activity as well as relaxin variants obtained by addition, substitution, or deletions of one or more relaxin components (conservative modifications).

"Therapeutically effective" refers in this context to the amount of pharmaceutically active relaxin that will result in a measurable desired medical or clinical benefit to a patient, as compared to the patient's baseline status or to the status of an untreated or placebo-treated (e.g., not treated with relaxin) subject. The terms "effective amount" and "effective dose" as used herein include within their meaning a non-toxic but sufficient amount or dose to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using routine experimentation.

The present disclosure shows that the administration of a therapeutically effective amount of relaxin can ameliorate the effects (glucotoxicity) of high blood sugar on beta-cells in the pancreatic islets of Langerhans and preserve beta-cell function. The corresponding method of treatment therefore reduces the risks of illness from obesity, overweight and weight gain. This pertains also to the concomitant risks of high blood pressure, high blood cholesterol, heart disease, stroke, breathing and cardiovascular problems and certain types of cancer and arthritis. Said illnesses are prevalent in persons suffering from impaired glucose tolerance (IGT), insulin resistance (IR) or manifest type-2 diabetes. The described methods of treatment can be used in controlling the risks of obesity. The disclosure further relates to a treatment of severely obese persons having a BMI of 35 or higher.

The terms "treating", "treatment", "preventing" and "prevention" refer in this context to any and all uses or administrations which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. Similarly, "prevention" does not necessarily mean that the subject will not eventually contract a particular condition or disease. Rather, "prevention" encompasses reducing the severity of, or delaying the onset of a particular condition or disease. In the context of some conditions, methods of the present invention involve "treating" the condition in terms of reducing or eliminating the occurrence of a highly undesirable and irreversible outcome of the progression of the condition but may not of itself prevent the initial occurrence of the condition. Accordingly, treatment and prevention include amelioration of the symptoms of a particular condition or preventing or otherwise reducing the risk of developing a particular condition.

The disclosure further pertains to the administration of relaxin to a patient afflicted of impaired glucose tolerance or highly in risk of impaired glucose tolerance with an amount of relaxin effective for protecting beta-cells and beta-cell function against the effects of high blood sugar levels. This encompasses a pharmaceutical composition comprising relaxin in a formulation for prolonged release of relaxin into the circulation. The slow-release composition is preferably formulated for subcutaneous injection, which shall not exclude any other administration by intravenous, intramuscular or intraperitoneal injection. A person skilled in the field will also contemplate formulation for transdermal, mucosal or oral administration of relaxin or even devices such as osmotic pumps for continuous delivery of relaxin into the blood stream.

The relaxin peptide is most preferably be compounded in a slow-release formulation for achieving serum levels in the range from 100 to 5000 pg relaxin per millilitre serum, preferably from 500 to 1000 pg relaxin per millilitre serum for a prolonged period of time from one day to six months or even longer.

The relaxin composition and the method of treatment may be based on a prodrug or derivative of relaxin or a protein chimera which is proteolytically processed to give rise to biologically active relaxin (cf. EP08844906, EP2215114). As relaxin is an insulin-like peptide it is therefore obvious to construct relaxin analogues similar to the currently studied slow-release insulin analogues. The relaxin is preferably synthetic relaxin (IFP GmbH, Hannover, Del.) or may be synthesized as described in EP10732429. The synthetic relaxin may comprise whole or part of the polypeptide sequence of the relaxin A-chain, the relaxin B-chain, and a methionine oxide analogue of the relaxin A-chain, a methionine oxide analogue of the relaxin B-chain. Alternatively, the relaxin may be derived from preprorelaxin or prorelaxin or obtained by a combination of separately produced A- and B-chains (cf. EP 0707650, Gold et al. (1992) Abstr. Pap. Chem. Soc. 203 Meet., Pt. 3, BTEC55). Human relaxin and analogues thereof are preferred.

The cDNA of human relaxin-2 (H2 relaxin) encodes a single-chain 23 kDa preprorelaxin comprising a signal peptide, a B-chain, a connecting C-peptide, and an A-chain (B-C-A). The signal peptide is cleaved off upon translation and translocation of the peptide into the endoplasmic reticulum producing a 19-kDa prorelaxin which is further processed in vivo by endoproteolytic cleavage of the C-peptide after the formation of disulfide bridges between the B- and A-chains in a manner analogous to insulin. In its mature form, human relaxin comprises two disulfides bridging the A- and B-chains at positions A9-B10 and A22-B22 as well as an intra-chain disulfide bridge in the A-chain at positions A8-A13 (cf. U.S. Pat. Nos. 4,656,249, 5,023,321; 4,871, 670; EP 0 101,309; EP 0 112,149; U.S. Pat. No. 4,565,249; AU 561,670; Haley et al. (1982) DNA 1:155-162; Stewart et al., NAR (1983) 11(19): 6597-660).

As used herein the term "derived" in the context of relaxin A and B chains means that the A and B chain sequences correspond to, originate from, or otherwise share significant sequence homology with naturally occurring A and B chain sequences. Thus, for example, a relaxin B chain present in a modified polypeptide may be identical to the B chain sequence of a relaxin from any species, such as the human H1 or H2 relaxin or may be a modified version or variant thereof. Alternatively, the B chain in a modified polypeptide may share sequence homology with one or more B chain sequences from any species. In humans three distinct forms of relaxin have been identified to date, H1, H2 and H3. Two distinct forms of relaxin (Rlx-1 and Rlx-2) have so far been isolated from vertebrates and vertebrate relaxin-1 (Rlx-1) corresponds to human relaxin-2 (H2-Rlx), whereas vertebrate Rlx-2 corresponds to H3 relaxin. Each of these forms is considered herein as a different "naturally occurring" relaxin.

Fully synthetic human relaxin is preferred for reasons of safety. The A- and B-chains of biologically active relaxin may have one or more methionine oxide residues or one or more methionine sulfoxide residues to ensure correct folding and combination of the chains. The relaxin may be one with human relaxin 1 wherein the B-chain is Met(0)24RLX1B or human relaxin 2 and the B-chain is Met(0)25RLX2B. A skilled person will also contemplate a synthetic polypeptide comprising: i) whole or part of a polypeptide sequence of synthetic relaxin 1 or synthetic relaxin 2 or ii) a polypeptide sequence derived from a different relaxin or a relaxin having a conservative amino acid substitution. In other words, the modified relaxin polypeptides must still bind to their receptors.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. The nature of other conservative amino acid substitutions is well known to those skilled in the art.

In the composition for administration, the relaxin peptides are preferably compounded or adsorbed or encapsulated in a slow-release formulation for achieving therapeutically effective serum levels in the range from 100 to 5000 pg Rlx/ml, preferably from 500 to 1000 pg Rlx/ml for prolonged periods of time from one day to six months or even longer. Slow-release compositions ensuring therapeutically effective relaxin levels in serum from one to six months are preferred. The slow-release compositions may be based on a biodegradable matrix or hydrogel comprising polyesters capable of immobilizing relaxin and other water-soluble macromolecules. As the ester linkages cleave, the entrapped relaxin is gradually released into the surrounding environment and into circulation. The rate of hydrolysis and concomitant relaxin release can be controlled by constructing polyesters containing varying proportions of esters activated by electron-drawing substituents vicinal to the ester function and/or by varying cross linking. Such relaxin-containing hydrogels or matrixes may be fabricated as microspheres that can be suspended in isotonic solutions and passed through a hypodermic needle, e.g. an 18- or 22-gauge hypodermic needle. Other slow-release compositions may be formulated with adsorbents, namely cellulosic adsorbents, polymeric adsorbents, e.g. certain polyacrylonitriles (e.g. as produced by Mitsubishi Rayon Company Limited), immuno-adsorbents (cross linked polyvinyl alcohol gels) or activated carbon (product of Toyobo Co., Ltd.). Such forms of slow-release administration may help to increase the patient compliance and the therapeutic effect.

A preferred method of treatment comprises the administration of human relaxin to a person afflicted of impaired glucose tolerance or in risk of becoming afflicted of impaired glucose tolerance in a dosis to achieve relaxin levels of 100 to 5000 pg/ml in serum. The dose range is adjusted to offset the glucotoxic effects of high blood sugar on pancreas, namely insulin cells, beta cells and beta cell function, and to ensure regular insulin secretion to match the changing metabolic demands of the body. Thus, therapeutically effective relaxin levels in serum prevent loss of beta-cells and beta-cell function and have beneficial effects in the regulation of blood sugar levels if a person is at risk of dysglycaemia or suffering from insulin resistance and impaired glucose tolerance. The disclosure provides in the broadest sense pharmaceutical compositions comprising relaxin and a suitable pharmaceutical excipient or diluent for reducing the glucotoxic effects of blood sugar on the pancreas function, insulin cells, beta cells and beta cell function. Preferred embodiment relate to compositions for subcutaneous injection in a method of treatment of persons highly at risk of becoming afflicted of impaired glucose tolerance or already suffering from impaired glucose tolerance to ameliorate the toxic effects of high blood sugar and for ceasing the progress of the illness from a mild state of insulin resistance with or without impaired glucose tolerance to a manifest type-2 diabetes.

BRIEF DESCRIPTION OF THE DRAWINGS

The present invention is best understood when read in conjunction with the accompanying figures, which serve to illustrate the preferred embodiments. It is understood, however, that the invention is not limited to the specific embodiments disclosed in the figures.

DETAILED DESCRIPTION OF THE INVENTION

Figure 1A:
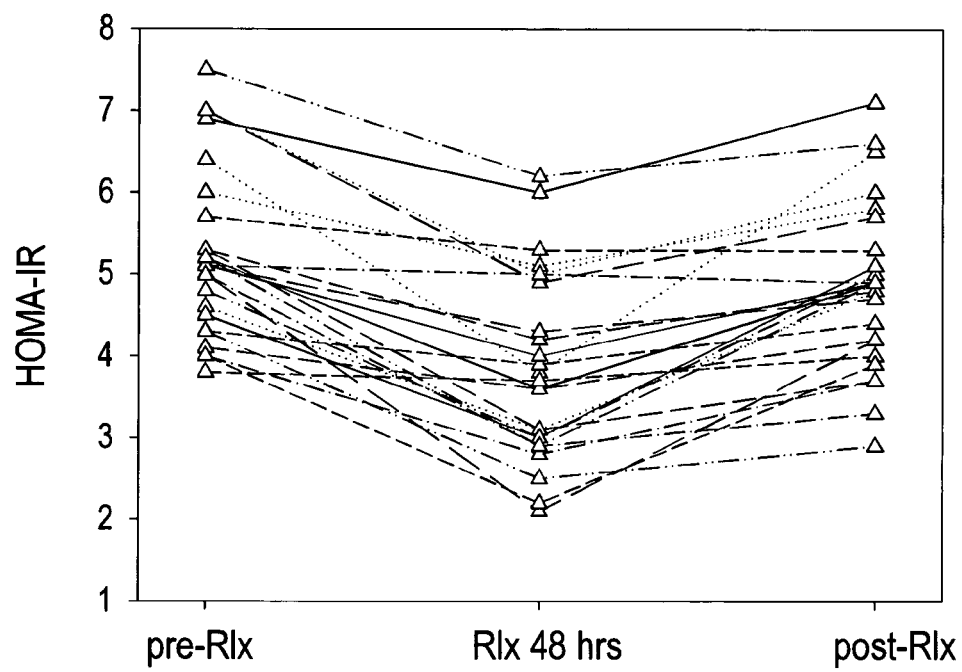
FIG. 1A is a diagram showing the individual homostasis model assessments (HOMA) of zucker diabetic fatty rats (ZDF rats) prior, during and post 48 hours s.c. administration of porcin relaxin (500 µg/kg and day)

Relaxin is a member of a protein hormone superfamily which includes insulin, insulin-like growth factors I and II (IGF-I and IGF-II), relaxin, and the insulin-like factors INSL3, 4, 5 and 6. In its mature form, relaxin is a heterodimeric peptide hormone wherein an A chain and a B chain are linked via disulphide bridges. Relaxin has been conserved through vertebrate evolution and can be found in a large and diverse range of vertebrate species which suggests a central, multifunctional role. Whilst in most species only two forms of relaxin have been identified (relaxin and relaxin-3), in humans three distinct forms of relaxin have been described. Of the three forms of relaxin in humans, H2 relaxin is the major stored form and the only form known to be secreted into the blood. The H1 form is largely restricted to the decidua, placenta and prostate, whilst H3 relaxin can be found in the brain. This suggests some differences in their biological roles, while all three forms display similar biological activity as determined, for example, by their ability to affect cAMP activity in cells expressing relaxin receptors, and accordingly share many biological functions in common. To date, H1, H2 and H3 relaxins have been shown to primarily recognise and bind four receptors, LGR7 (RXFP1), LGR8 (RXFP2), GPCR135 (RXFP3) and GPCR142 (RXFP4). LGR7 is the most widely expressed of these receptors and binds each of H1, H2 and H3 with high affinity. H1 and H2 relaxin also bind LGR8. H3 relaxin binds GPCR135 and GPCR142 in addition to LGR7.

The classical role of relaxin (H2 relaxin) is to regulate reproduction and parturition, namely to govern early implantation in pregnancy and to stimulate remodelling of connective and placental tissue. Additionally, relaxin induces the breakdown of collagen, one of the main components of connective tissue. However, it is now well established that relaxin also acts as an endocrine and paracrine factor, causes a widening of blood vessels (vasodilatation) in the kidney, mesocaecum, lung and peripheral vasculature, which leads to increased blood flow or perfusion rates in these tissues (Dschietzig T & Stangl K CMLS 2002; 59:1-13 (Review); Dschietzig T et al. Circ. Res. 2003; 92:32-40). The brain is another target tissue for relaxin where it has been shown to bind to receptors in the circumventricular organs to affect such diverse functions such as blood pressure, drinking, memory-related functions and addictive behaviours. Aberrant relaxin activity and/or expression has been implicated in a number of disorders and diseases such as cardiovascular diseases, renal diseases, fibrotic disorders (including cardiac fibrosis and fibrosis associated with airway remodelling), neurological disorders, immune diseases and endometrial and reproductive disorders.

Consequently, numerous clinical applications of relaxin and relaxin agonists and antagonists have been suggested, particularly for treating diseases related to vasoconstriction (EP07008840), as a co-factor or for replacement of insulin (EP1909809), to increase arterial compliance (EP05731443), for tumor suppression (EP07719531), as adjuvant in the differentiation of stem cells (EPO4806868), for increasing fertility (EP03005488) or a control of fetal growth (EP5780049, EP98932799), for modulating apoptosis, for treating neurodegenerative dysfunctions (EP99948802, EP0919297), for promoting angiogenesis, as well as even for promotion of hair growth and inhibition of cutaneous aging (EP0793505).

Here we disclose a use of relaxin to inhibit, prevent or ameliorate the toxic effects of high blood sugar on beta-cells in the islets of Langerhans and to restore beta-cell function and thus for treatment of persons in risk or afflicted of impaired glucose tolerance (IGT). Impaired glucose tolerance is prevalent in obese or overweight persons and represents a defined state of dysglycaemia in which the subject does not yet require insulin but wherein the glucotoxicity of high blood glucose will effect a loss of beta-cells and beta-cell function so that the disease will progress to a manifest type-2 diabetes. Relaxin has so far not been tested as to its effects on beta-cells. It was only known that plasma concentrations of endogenous relaxin in women newly diagnosed of type-2 diabetes correlate positively to insulin sensitivity and negatively to beta-cell function (Szepietowska B et al (2008), *Diabetes Research and Clinical Practice,* 79(3): e1-e3p). However, these data relate to women having manifest type-2 diabetes. The plasma relaxin concentrations were further related to parameters such as body mass index (BMI), blood pressure, parameters of metabolic control (fasting glucose level, HbA1c, total HDL and LDL cholesterol, triglycerides) and insulin resistance according to HOMA 2. Pregnant women with increased serum levels of relaxin were excluded in that study. In pregnant women having type-1 diabetes, serum relaxin concentrations are also significantly elevated but the data show no significant correlation with mean daily glucose, HbA1, insulin levels, IGF-1, hPL, hCG, estradiol-17β or progesterone (Whittaker P G et al. (2003) *Abnormal relaxin secretion during pregnancy in women with type* 1 *diabetes*, Exp. Biol. Med.: 228, 33-40). Moreover, other members of the insulin-like peptide family also play important roles in glucose control because a beta-cell specific deletion of the IGF-I receptor leads to hyperinsulinemia and glucose intolerance. A functional inactivation of the IGF-I receptor in skeletal muscle causes glucose dysregulation.

The present disclosure relates to pharmaceutical compositions and methods of treating impaired glucose tolerance (IGT). Impaired glucose tolerance (IGT) is a pre-diabetic state of dysglycaemia and associated with insulin resistance and increased risk of cardiovascular pathology. IGT precedes type-2 diabetes mellitus by many years and is a major risk factor for mortality. According to the criteria of the World Health Organization and the American Diabetes Association, impaired glucose tolerance is defined as two-hour glucose levels of 140 to 199 mg per dL (7.8 to 11.0 mmol) on the 75-g oral glucose tolerance test. This is a medical test in which glucose is given and blood samples taken afterward to determine how quickly it is cleared from the blood. The test is usually used to test for diabetes, insulin resistance, and sometimes reactive hypoglycaemia or rarer disorders of carbohydrate metabolism. In the most commonly performed version of the test, an oral glucose tolerance test (OGTT), a standard dose of glucose is ingested by mouth and blood levels are checked two hours later. Many variations of the GTT have been devised over the years for various purposes, with different standard doses of glucose, different routes of administration, different intervals and durations of sampling, and various substances measured in addition to blood glucose. A patient is said to be under the condition of IGT when he or she has an intermediately raised glucose level after 2 hours, but less than would qualify for type-2 diabetes mellitus. The fasting glucose may be either normal or mildly elevated.

While having not found any direct effect on glucose levels in blood we have discovered that the administration of relaxin has the beneficial effect of preventing the high glucose-induced down-regulation of insulin secretion (glucotoxicity) in cells. In other words, the provision of external relaxin is advantageous over current medications such as with metformin because it prevents a loss of beta-cell function and may even re-establish beta-cell functions so that its administration can be included in a therapy for preventing prediabetic patients or patients in risk of IGT to move on from this state of dysglycaemia to a manifest type-2 diabetes. In other words, if a patient develops insulin resistance on a hereditary background or metabolically driven by obesity and sedentary lifestyle, the increased insulin demand is entirely compensated initially by an increased secretion of insulin from the pancreatic beta-cells. However, since high insulin levels promote adipogenesis, which, in turn, further impairs via adipocytokines insulin sensitivity, glucose levels will eventually rise. The toxicity of high glucose levels on beta-cells and the decreasing insulin sensitivity will take their toll and the person in question will eventually develop a manifest type-2 diabetes. The administration of relaxin to such patients in risk of type-2 diabetes can therefore prevent this progress.

Furthermore, diabetic end-organ damage (diabetic nephropathy and cardiomyopathy, peripheral arterial disease) may become mitigated since they correlate both with hyperinsulinemia (insulin resistance) and glucotoxicity. The administration of relaxin therefore reduces health risks associated with obesity, hypertension and dyslipidemia (the metabolic syndrome). During treatment with relaxin no clinically adverse effects were observed over the entire dose range in a previous pilot study related to cardiovascular diseases (Dschietzig et al., J Cardiac Fail. 2009; 15:182-190).

Without wanting to be bound by theory, relaxin is a circulating hormon that improves heart and renal function via specific and balanced vasodilation. This activity has been physiologically confirmed for human relaxin H2. Thus, it can be assumed that the beneficial anti-glucotoxic effects of relaxin on pancreas and particularly on cells of the islets of Langerhans can be found for all types of relaxin polypeptides, namely for H2 preprorelaxin, prorelaxin, and relaxin; other vertebrate analoga such as H1 and H3 preprorelaxin, prorelaxin, and relaxin; biologically active relaxin from recombinant, synthetic or native sources as well as relaxin variants such as conservative amino acid sequence variants. A person skilled in this field will further contemplate active agents with relaxin-like activity such as relaxin agonists and/or relaxin analogues and portions thereof that retain biological activity, including all agents that competitively displace bound relaxin from its receptor, in particular from the LGR7 receptor (RXFP1). Also encompassed is relaxin modified to increase its in-vivo half-life, e.g., PEGylated relaxin (i.e., relaxin conjugated to a polyethylene glycol), modifications of amino acids in relaxin that are subject to cleavage by degrading enzymes, and the like. Preferably, any modification of relaxin amino acid sequence or structure is one that does not increase its immunogenicity in the individual being treated with the relaxin variant.

Slow-release compositions are for example those as in Swiss patent CH 679 207 A5. In essence, in may be preferred to have the relaxin compounded or trapped for slow release in degradable "microparticles" which have to be understood as solid objects of any shape, e.g. microspheres or microgranules having a median diameter of less than 250 micrometers. It is possible to achieve with such degradable microparticules a continuous and efficient slow release of the active relaxin during at least a period of 3 to 6 months after injection of the composition. To this effect a pharmaceutical composition made of microparticles is contemplated for the slow release of biologically active relaxin at least during a period covering the $3^{rd}$ or $6^{th}$ month after injection. Said slow-release composition may therefore comprise a group of microparticles made of a copolymer of the PLGA type which incorporate relaxin in the form of a water-insoluble peptide salt. In a preferred embodiment, the slow-release composition comprises one single group of microparticles. However, in order to achieve a constant relaxin concentration in the circulation over an extended period of time a mixture of defined smaller and larger microparticles is preferred as smaller microparticles possible degrade and release faster, whereas larger microparticles will become degraded at a later stage. However, the mixture of relaxin-containing degradable microparticles may also consist of different co-polymers, which partly be encapsulated, to achieve a prolonged continuous release of relaxin.

The microparticles may be microspheres or microgranules. The composition may typically comprise a group of microparticles wherein the lactide content of the PLGA is of at least 85%. Said biodegradable polymers or copolymers may be selected from the group consisting of polyglycolide, poly(L-lactide-co-glycolide), poly(D,L-lactide-co-glycolide), poly(L-lactide), poly(D,L-lactide), poly(L-lactide-co-D, L-lactide), polycaprolactone, poly(L-lactide-co-caprolactone), poly(D, L-lactide-co-caprolactone) polytrimethylenecarbonates, poly(L-lactide-co-trimethylenecarbonate), poly(D,L-lactide-co-trimethylenecarbonate), polydioxanones, polylactic acid polymers, polyglycolic acid polymers, copolymers of polylactic acid and polyglycolic acid, polyhydroxybutyrates, polyhydroxyvalerates polydioxanones, polyorthoesters, polycarbonates, polytyrosinecarbonates, polyorthocarbonates polyalkylene oxalates, poly-alkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof. The relaxin is preferably compounded as an organic salt which is preferably a dispersing agent or plasticizer of the biodegradable polymer or copolymer. The organic compound may be selected from the group consisting of N-isopropylpyrrolidone, N-methylpyrimidine, N-ethylpyrimidine, N-methylpyrrolidone (1-methyl-2-pyrrolidone), N-ethylpyrrolidone, N-propylpyrrolidone, N,N-diethyl-1,4-butane-diamine, 1-(2-aminoethyl)-piperazine, 2-(1-pyrrolidyl)ethylamine, 4-amino-2-methoxy-pyrimidine, 2-dimethylaminoethanol, 1-(2-hydroxyethyl)-piperazine, 4-(2-hydroxyethyl)-morpholine, 2-mercaptopyrimidine, 2-mercaptobenzimidazole, N,N-dimethyl-1,3-propanediamine, 4-(2-aminoethyl)-pyridine, 2-amino-6-methoxybenzothiazole, 4-(amino-ethyl)pyridine, N,N-diallylmelamine, 3-amino-1,2,4-triazole, 1-(3-aminopropyl)-imidazole, 4-(2-hydroxyethyl)-pyridine, 1-(2-hydroxyethyl)-imidazole, 3-mercapto-1,2,4-triazole.

In accordance with the invention, said biodegradable polymer may be a copolymer of polylactic acid and polyglycolic whose composition is 50 to 80 percent lactic acid and 20 to 50 percent glycolic acid. Said PLA: PGA co-polymer may have a selected weight average molecular weight range between about 25 000 and about 1 000,000. The invention further extends to biodegrable polymer composition comprising a polymer matrix of resorbable polymer(s) or copolymer(s), and a pharmaceutically effective amount of relaxin polypeptides, preferably H2 relaxin.

EXAMPLES

Example 1

Effect of sc RlX on HOMA-Index in ZDF Rats

The homeostatic model assessment (HOMA=Insulin (µU/ml)×Glucose (mmol/l)/22.5) allows a quantification of insulin resistance and beta-cell function on the basis of mathematical equations describing glucose regulation as a feedback loop (see Matthews D R at al. Diabetologia 1985; 28(7): 412-9); Turner R C et al, Metabolism 1985; 28 (11): 1086-96). In order to assess the effects of relaxin on a diabetic metabolism we determined the HOMA of 10-week old male Zucker Diabetic Fatty rats (#25) pre-, during and post subcutanous administration of porcine relaxin (500 µg/kg rat per day). Thus, we determined the glucose and insulin levels in serum of 25 ZDF rats prior and 48 hours after sc administration of porcine relaxin. This was completed by follow-up determinations of glucose and insulin concentrations in serum 48 hours post the termination of the administration of porcine relaxin. The respective results for the HOMA values are shown in FIGS. 1A and B.

Figure 1B:
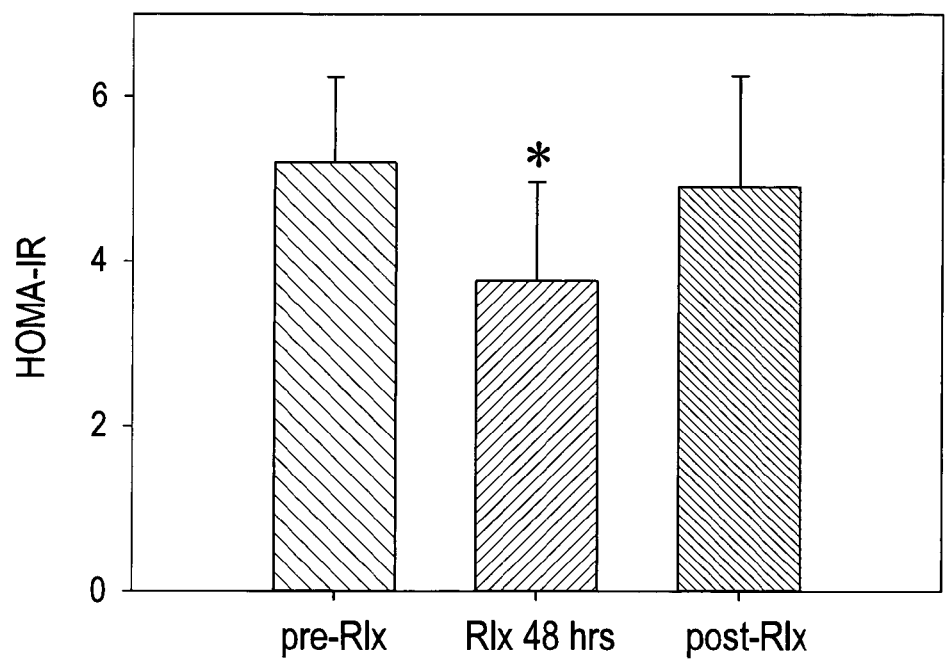
FIG. 1B is a diagram showing the HOMA data of FIG. 1A as mean values and respective standard deviations in accordance with Friedman ANOVA on ranks, followed by Dunnett's test.

FIG. 1A confirms that a sc administration of relaxin produced in each animal a reduced HOMA value within the 48-hour period. FIG. 1 B shows the respective HOMA data as mean values and standard deviations analysed with Friedman ANOVA on ranks, followed by Dunnett's test, using the SPSS 8 program software. The data confirms that the substantive effect of porcine RLX on the HOMA value is statistically significant in rat.

Example 2

Effect of H2 RLX on HOMA-Index in Human Patients

In a study approved by the local ethical committee (Charité, Berlin, Germany) twelve patients (n=12) having type II diabetes or impaired glucose tolerance received intravenous synthetic H2 relaxin over a period of 16 hrs followed by a 24-hr follow-up. The anti-diabetic treatment of those patients was not varied. The improved HOMA-2 model used was in the present example because it reflects better human physiology. A HOMA of >2 indicates a potential insulin resistance; a HOMA of >2.5 beginning insulin resistance and a HOMA>5.0 is an average value of insulin resistance in untreated patients with manifest type-2 diabetes.

Of those twelve patients in this study two patients received sequential treatment for 8 hours each with dosages equivalent to 10 and 30 µg/kg of subject body weight per day, 6 patients received sequential treatment with 240 and 480 µg/kg of subject body weight per day, and another 4 patients received a constant infusion of 960 µg/kg of subject body weight per day. This was completed by follow-up determinations of glucose and insulin levels in serum 24 hours post termination of the i.v. relaxin administration. The results are shown in FIGS. 2A and B.

Figure 2A:
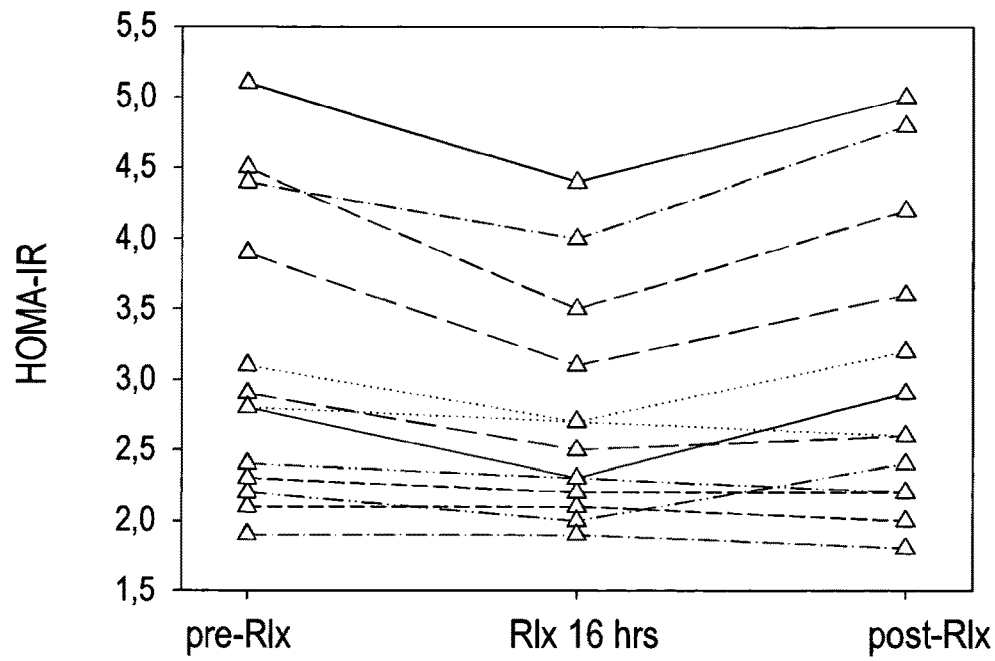
FIG. 2A is a diagram showing individual homeostasis model assessments (HOMA) of diabetic patients pre, during and post 16 hours i.v. administration of different dosis of H2 relaxin (HOMA=insulin (µU/ml)×glucose (mmol/l)/22.5; wherein HOMA>2 indicates a likely insulin resistance; HOMA>2.5 a manifest insulin resistance and HOMA>5.0 represents an average value found in type-2 diabetes)
Figure 2B:
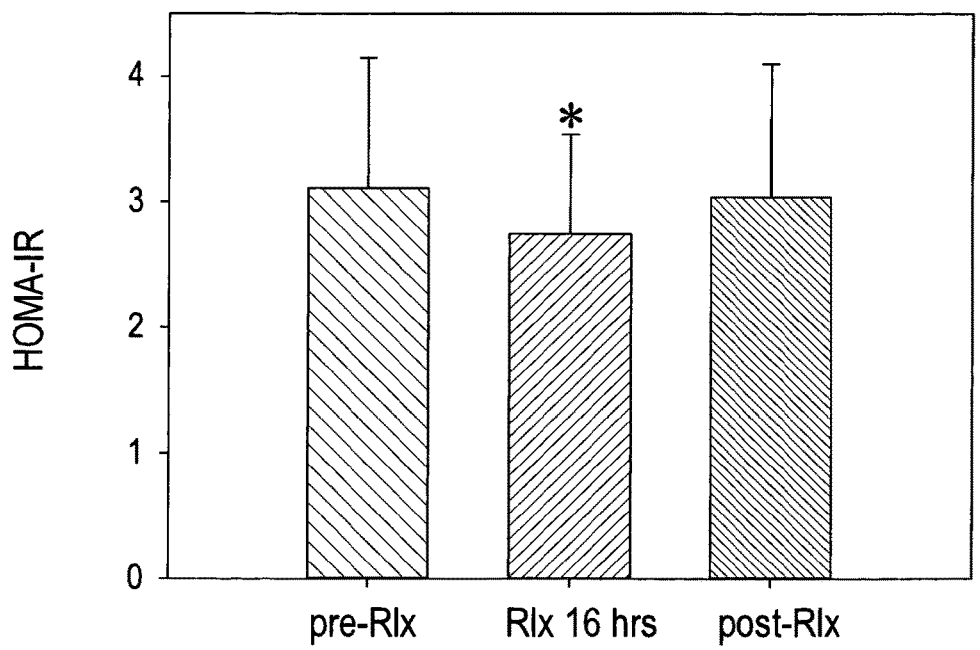
FIG. 2B is a diagram showing the HOMA data of FIG. 2A as mean values and respective standard deviations in accordance with Friedman ANOVA on ranks, followed by Dunnett's test.

FIG. 2A confirms that the administration of i.v. H2 relaxin improved in each diabetic patient the homeostatic model assessment, effectively increasing the response to insulin, whereas H2 relaxin had no or little impact on homeostatic model assessment in non-diabetic subjects having an initial HOMA of less than 2.0. The data therefore suggests that H2 relaxin is efficient in preventing the glucose-induced down-regulation of the insulin effect. FIG. 2B shows the respective HOMA data as mean values and standard deviations in accordance with Friedman ANOVA on ranks, followed by Dunnett's test. The data confirms that H2 RLX has a significant effect on the homeostatic model assessment (HOMA) in man as all diabetic patients improved in insulin sensivity during relaxin treatment.

Example 3

Influence of Sustained Glucose Concentration on the Function of Beta-Cells and Their Secretion of Insulin into the Supernatant In a further study we examined whether porcine relaxin has any effect on insulin expression and/or secretory capacity of pancreatic beta-cells. $2.5 \times 10^5$ rat insulinoma cells (INS-1 cells; see Mergler S et al, in *Cellular Signalling* (2008), doi: 10.1016/j.cellsig.2008.08.015) were plated in a 24-well plate and grown for three days in RPMI-640 medium with supplements (Moore G. E. et. al., *Culture of Normal Human Leukoctyes."* JAMA, v. 199, 519-524 (1967). On the day of the experiment, the medium was removed, and the INS-1 cells were washed three times and then preincubated for 30 min in KRB (Krebs-Ringer buffer: 115 mM NaCl, 5.9 mM KCl, 1.2 mM $MgCl_2$, 1.2 mM $NaH_2PO4$, 1.2 mM $Na_2PO_4$, 2.5 mM $CaCl_2$, 25 mM $NaHCO_3$, pH 7.4) comprising 0.5% BSA and 3.3 mM glucose. Cells were washed again with phosphate buffered saline (PBS: 137 mM NaCl, 2.7 mM KCl, 12 mM phosphate, pH 7.4) and incubated with different physiological and pathological glucose concentrations (2.8, 5.6, 11.2, 16.7, 33.2 mmol/L) for 48 hrs. After another washing, the amounts of insulin secreted by the INS-1 cells into the supernatant over another 48 hrs under the very same glucose conditions were determined using a rat insulin ELISA kit (units: ng/dl) (Immundiagnostik AG, Bensheim, Del.—Article No. KA80INSRT1).

In a parallel set, 10 nmol/L (60 ng/ml) porcine relaxin-1, an analogue to H2 relaxin, was added to the supernatant of the cell culture. 10 nmol/L relaxin corresponds to the physiological relaxin concentration in a pregnant rat. The porcine relaxin-1 was a gift of Sherwood OD (University of Illinois, Urbana, USA) and its purification encompassed acetone precipitation, gel filtration, and ion exchange chromatography (Sherwood, OD in *Isolation and characterization of porcine and rat relaxin. Adv. Exp. Med. Biol.* (1982) 143: 115-147).

Figure 3:
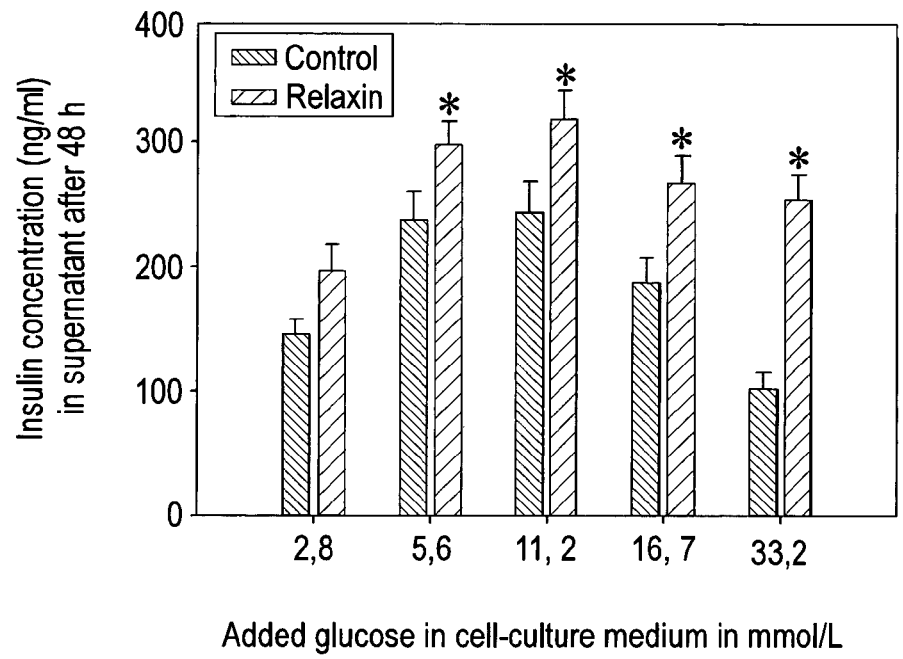
FIG. 3 is a diagram showing the glucotoxic effect of high blood sugar (high glucose concentration in serum) on rat insulin cells (INS-1 cells)—i.e. prolonged elevation of insulin is suppressing insulin secretion—in the presence and absence of porcine relaxin-1 (the analogue to human relaxin H2)
Figure 4:
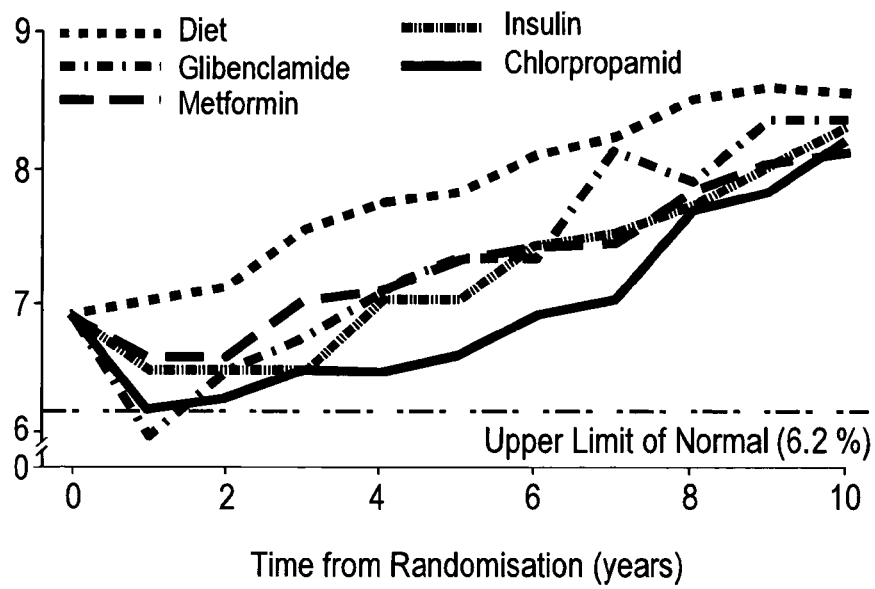
FIG. 4 is a diagram showing serum HbA1c levels of patients receiving conventional medication over several years.

The results have been summarized in FIG. 3. Thus, the data indicates that relaxin is efficient in preventing the high glucose-induced down-regulation of insulin expression and/or the secretory capacity of cultured rat INS-1 cells (insulinoma cells). Number of experiments=6 each; *, P<0.05 vs. control.

The data shows increased insulin secretion (as determined in cell supernatants) in the presence of 10 nM of relaxin, both at baseline and under high-glucose conditions, for a secretion period of 48 hours. Thus, relaxin is efficient in preventing the high glucose-induced down-regulation of insulin expression and/or secretory capacity in cultured rat INS-1 cells (insulinoma cells). Pancreatic beta-cells must be capable of secreting thousands of proteins per second and to accomplish this they contain a highly developed endoplasmic reticulum (ER) where newly synthesized proteins fold and assemble to native structures before secretion. Without being bound by any theory, it seems that the activity of relaxin is related to the ER-associated degradation (ERAD) of misfolded proteins in secretory cells as the loss of the beta-cell secretory capacity by the toxic effects of high glucose levels in serum corresponds with the observable increase of incompletely processed insulin, say with an increase secretion of incorrectly processed proinsulin, and therefore with the malfunction of protein biogenesis. If ERAD is insufficient, misfolded proteins accumulate causing ER stress, apoptosis, and ER storage diseases. The capacity of ERAD therefore critically determines the efficiency of protein secretion and beta-cell function and preservation of beta-cells.

The data of examples 1 to 3 support a combination of effects, namely a prevention of beta-cell function, as shown by the experiment with INS-1 cells, and in the homeostatic model assessments an increased insulin sensitivity which is likely due to a higher proportion of correctly processed and secreted insulin molecules, instead of inactive proinsulin peptides, so that these combinatory effects can be used for new therapy for preventing subjects afflicted of a state of disglycaemia or having impaired glucose tolerance (IGT) to progress to a state of a manifest type-2 diabetes. Thus, there is good evidence that sc or iv administration of relaxin prevents the progress of the disglycaemia to type-2 diabetes and ameliorates the side effects of excessive insulin therapy (weight gain, adipogenesis). Furthermore, diabetic end-organ damage (diabetic nephropathy and cardiomyopathy, peripheral arterial disease) is expected to be mitigated since it correlates both with hyperinsulinemia (insulin resistance) and with increased plasma glucose (glucotoxicity).

Example 4

Slow-Release Formulation of Relaxin

The therapeutic advantage of RLX seems that it mediates and stimulates correct insulin secretion and mitigates the toxic effects of high glucose levels on beta-cells and beta-cell function, while not directly affecting glucose levels such as prior art drugs. However, the limiting factor in diabetes treatment seems its half-life in vivo, which is about two hours only. Which enzymes are involved remains to be elucidated while dipeptidylpeptidase IV (DPP IV) is a hot candidate. DPP IV clears the two N-terminal amino acids from relaxin. Therefore, relaxin has to be continuously infused or repetitively injected in order to achieve therapeutic efficacy. Therefore, a sustained-release delivery system for relaxin over several days or weeks is highly desirable for treatment of IGT and person afflicted of disglycaemia.

Injectable and biodegradable microspheres (MS) have been widely studied in recent years and have become well established controlled drug delivery systems. The poly(D, L-lactic-co-glycolide) (PLGA 48:52 to 48:52 molar ratio, molecular weight 35 kDa, Resomer® RG503H) was purchased from Evonik Röhm GmbH, Darmstadt (Germany). 2 mg of porcine RLX and 10 mg PVP were dissolved in 1 ml distilled water by sonication in a water bath. 100 mg of PLGA in 1 ml acetonitrile was added and the mixture for 10 minutes at room temperature and lyophilized at 20° C. for 1 hours. The microspheres were then washed three times in petrol ether and lyophilized at −20° C. and 0.1 mPa overnight.

The bioactivity of the relaxin microspheres in ZDF rats is to be tested by injecting relaxin microspheres intraperitoneally or subcutaneously.

The invention claimed is:

1. A method of treatment of a subject suffering from an increased homeostatic model assessment (HOMA) value and having a body mass index greater than 25, which subject is not suffering from diabetes, comprising the steps of:

obtaining at least one sample of serum from said subject, performing a homeostatic model assessment (HOMA) based on said at least one sample of serum, and if a HOMA value of >2 is obtained, performing at least one test for diagnosis of diabetes based on said at least one sample of serum, and if said subject does not suffer from type II diabetes, administering subcutaneously an effective amount of full-length synthetic H2 relaxin to said subject, at a dose to achieve 100 to 5000 pg full-length synthetic H2 relaxin per milliliter serum, to prevent a high glucose-induced down-regulation of the insulin secretion in beta-cells and to protect beta-cells and beta-cell function.

2. A method of utilizing full-length synthetic H2 relaxin in a subcutaneously applicable pharmaceutical composition with a dosage to achieve 100 to 5000 pg full-length synthetic H2 relaxin per milliliter serum for the treatment of a subject suffering from an increased homeostatic model assessment (HOMA) value of >2, which subject is not suffering from type II diabetes, to prevent a high glucose-induced down-regulation of the insulin secretion in beta-cells and to protect beta-cells and beta-cell function.

* * * * *